(12) United States Patent
Gutfinger et al.

(10) Patent No.: US 7,976,551 B1
(45) Date of Patent: Jul. 12, 2011

(54) TRANSSEPTAL DELIVERY INSTRUMENT

(75) Inventors: Dan E. Gutfinger, Irvine, CA (US);
Paul Hindrichs, Plymouth, MN (US);
Phong D. Doan, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 783 days.

(21) Appl. No.: 11/763,290

(22) Filed: Jun. 14, 2007

(51) Int. Cl.
*A61B 19/00* (2006.01)
(52) U.S. Cl. ...................................................... 606/129
(58) Field of Classification Search .................. 606/108, 606/184, 129; 600/372–375; 607/119–122; 604/532, 530, 510
See application file for complete search history.

(56) References Cited

U.S. PATENT DOCUMENTS

| | | | |
|---|---|---|---|
| 6,185,464 B1 * | 2/2001 | Bonner et al. | 607/119 |
| 6,328,699 B1 * | 12/2001 | Eigler et al. | 600/486 |
| 6,695,793 B2 * | 2/2004 | Brennan et al. | 600/585 |
| 2002/0007205 A1 * | 1/2002 | Zheng et al. | 607/122 |
| 2004/0039371 A1 * | 2/2004 | Tockman et al. | 604/528 |
| 2004/0225297 A1 * | 11/2004 | Chen | 606/108 |
| 2006/0036307 A1 * | 2/2006 | Zarembo et al. | 607/122 |
| 2006/0041300 A1 | 2/2006 | Zhang et al. | |
| 2006/0136026 A1 * | 6/2006 | Zheng et al. | 607/122 |
| 2006/0196137 A1 | 9/2006 | Brenzel et al. | |
| 2006/0200197 A1 * | 9/2006 | Brenzel et al. | 606/213 |
| 2006/0293643 A1 * | 12/2006 | Wallace et al. | 606/1 |
| 2007/0225681 A1 * | 9/2007 | House | 604/528 |

\* cited by examiner

*Primary Examiner* — Gary Jackson
*Assistant Examiner* — Christopher Schubert

(57) ABSTRACT

Access to the left side of the heart is gained through a heart wall. A delivery instrument includes a guide that may include or carry a puncturing instrument that is adapted to be directed toward the heart wall. In some embodiments a distal portion of the delivery instrument may be adapted to be co-located with the coronary sinus. In addition, the guide may be located a known distance from the portion of the delivery instrument that is co-located with the coronary sinus. Access to the left side of the heart may thus be readily gained by positioning the delivery instrument relative to the coronary sinus.

16 Claims, 16 Drawing Sheets

TRANSSEPTAL DELIVERY INSTRUMENT

TECHNICAL FIELD

This application relates generally to implantable cardiac devices and, in some embodiments, to a transseptal delivery apparatus for and a transseptal method of accessing a left side of a heart.

BACKGROUND

When a person's heart does not function normally due to, for example, a genetic or acquired condition, various treatments may be prescribed to correct or compensate for the condition. For example, pharmaceutical therapy may be prescribed for a patient or a pacemaker or similar device may be implanted in the patient to improve the function of the patient's heart.

In conjunction with such therapy it may be desirable to detect conditions in or apply therapy to one or more chambers of the heart. For example, an implanted device may sense electrical activity in a chamber and, based on the sensed conditions, apply an electrical stimulus to a chamber. Similarly, an implanted device may measure cardiac pressure in a given chamber in an attempt to determine how the heart is functioning. Then, based on the pressure reading, the patient's therapy may be modified to compensate for any undesirable conditions. For example, if cardiac pressure is measured over time, the operation of an implanted cardiac device such as a cardioverter defibrillator may be adjusted, as necessary, according to conditions diagnosed as a result of the pressure measurements.

Traditionally, access to one or more chambers of the heart has been gained via the venous system. That is, a cardiac lead is inserted into a vein and then routed through the venous system to a chamber on the right side of the heart.

In some cases, however, it is desirable to sense conditions or provide treatment to a chamber on the left side of the heart. For example, left atrial pressure has been identified as a potential indicator for left ventricular failure. Access to the left side of the heart may be obtained from the right side of the heart by routing a lead through a septal wall that separates a right chamber from a left chamber. Accordingly, there is a need for an effective mechanism that provides access to the left side of the heart via a transseptal technique.

SUMMARY

A summary of various aspects and/or embodiments of an apparatus constructed or a method practiced according to the invention follows. For convenience, an embodiment of an apparatus constructed or a method practiced according to the invention may be referred to herein simply as an "embodiment."

The invention relates in some aspects to an apparatus or method for accessing the left side of a heart. For example, a delivery instrument may be routed through the venous system to the right side of the heart. Using the delivery instrument, a puncture may be made in a wall of the heart to gain access to the left side. An implantable device may then be inserted into or through the wall to, for example, acquire information from or provide therapy to the left side.

In some embodiments access to the left atrium is gained through the inter-atrial septum. Here, a portion of the delivery instrument may be adapted to be co-located with the coronary sinus. For example, in some embodiments the delivery instrument may include a protruding member that is adapted to rest on and/or around tissue adjacent the ostium of the coronary sinus. In some embodiments the delivery instrument may include one or more markers that may be sensed by an imaging apparatus. The imaging apparatus may thus be used to identify the position of the markers relative to the ostium of the coronary sinus.

The delivery instrument includes a guide that is used to gain access to the left atrium. For example, the guide may include or carry a puncturing instrument that is adapted to be directed toward the inter-atrial septum. To this end, the guide is located a known distance in a proximal direction from the portion of the delivery instrument that is co-located with the coronary sinus. By proper setting of this distance, the puncture may be readily made at a desired location in the inter-atrial septum.

In some embodiments the delivery instrument may be used to access a portion of the heart at or near the fossa ovalis. For example, the delivery instrument may be adapted (e.g., sized) so that once a distal portion of the delivery instrument engages the coronary sinus, the puncturing instrument may be readily (e.g. automatically) directed toward a wall of the heart at or near the fossa ovalis.

Through the use of such a delivery instrument, a physician may take advantage of his or her ability to access to the coronary sinus to readily gain access to the left atrium. Specifically, many physicians who regularly implant cardiac devices have extensive experience implanting leads via the coronary sinus. For example, to sense or stimulate the left side of the heart a physician may implant a lead through the coronary sinus. A physician may use these same skills to co-locate the delivery instrument located with the coronary sinus. At this point, the delivery instrument may automatically direct the puncturing instrument through the inter-atrial septum at a desired location, thereby potentially eliminating steps that the physician would otherwise use to determine where to puncture the inter-atrial septum.

Similarly, a physician may be able to use simpler and/or more cost effective imaging techniques since the physician may have a high level of confidence that the delivery instrument will pierce the inter-atrial septum at the desired location. For example, an implant procedure may be performed using, for example, only fluoroscopic guidance. Accordingly other techniques such as echocardiography may not be needed.

In some embodiments the delivery instrument also may be used to implant leads. For example, the delivery instrument may include one or more lumens for carrying (e.g., routing) a lead to an implant site (e.g., where the puncturing instrument created a hole). Thus, once a distal portion of the delivery instrument engages the coronary sinus and the puncturing instrument has created a hole, a distal portion of the lead may be routed through the delivery instrument and into the hole (e.g., in a septal wall, at or near the fossa ovalis, etc.).

In some embodiments the delivery instrument also may be used to implant leads via the coronary sinus. For example, the delivery instrument may include one or more lumens for carrying (e.g., routing) one or more leads into the coronary sinus to an implant site that provides sensing and/or stimulation for the left atrium and/or the left ventricle.

BRIEF DESCRIPTION OF THE DRAWINGS

These and other features, aspects and advantages of the invention will be more fully understood when considered with respect to the following detailed description, appended claims and accompanying drawings, wherein:

FIG. 15, including

Figure 1:
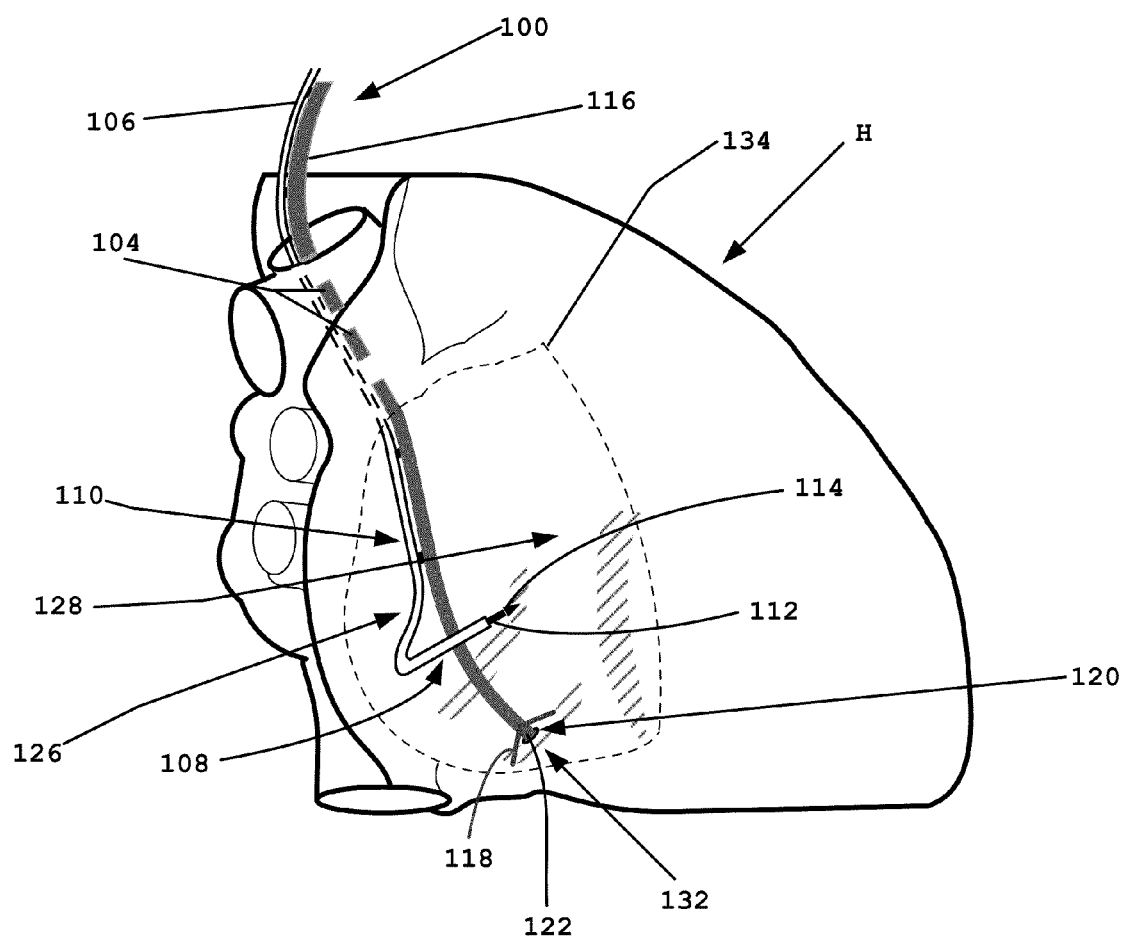
FIG. 1 is a simplified diagram of an embodiment of a delivery instrument positioned in a heart.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

The invention is described below, with reference to detailed illustrative embodiments. It will be apparent that the invention may be embodied in a wide variety of forms, some of which may appear to be quite different from those of the disclosed embodiments. Consequently, the specific structural and/or functional details disclosed herein are merely representative and do not limit the scope of the invention. For example, based on the teachings herein one skilled in the art should appreciate that the various structural and/or functional details disclosed herein may be incorporated in an embodiment independently of any other structural and/or functional details. Thus, an apparatus may be implemented and/or a method practiced using any number of the structural and/or functional details set forth in any disclosed embodiment(s). Also, an apparatus may be implemented and/or a method practiced using other structural and/or functional details in addition to or other than the structural and/or functional details set forth in any disclosed embodiment(s). Accordingly, references to "an" or "one" embodiment in this discussion are not necessarily to the same embodiment, and such references mean at least one embodiment.

FIG. 1 illustrates an embodiment of an apparatus 100 (referred to herein as a delivery instrument) that may be used to deliver one or more implantable leads or other devices to a heart H of a patient. In particular, the delivery instrument 100 may be used to implant a lead or other device through a wall of the heart H. For convenience, FIG. 1 only shows a distal portion of the delivery instrument 100 after it has been positioned in the heart H. It is to be understood that the instrument comprises a thin elongated structure that is adapted to be routed through the venous system and that a proximal end of the delivery instrument 100 may include various lumens and/or connectors to properly interface with and/or control the components at the distal portion. Also, the heart H is shown in a partially cutout view (as represented by a dashed line 134) to more clearly show the location of some of the components of the delivery instrument 100.

The delivery instrument 100 may be inserted into the heart H via a superior transvenous approach. For example, a distal portion of the delivery instrument 100 may initially be inserted into a vein near a subcutaneous implant site for an implantable cardiac device in a pectoral region of the patient (not shown in FIG. 1). The distal portion of the delivery instrument may then be routed through the venous system and into the heart via the superior vena cava 104.

The delivery instrument 100 includes an elongated, flexible component 106 (hereafter referred to as a "guide") that is used to gain access to the left side of the heart H. For example, the guide 106 may be adapted to provide an orientation where a distal end 108 of the guide 106 is directed to a heart wall such as the inter-atrial septum 110 as shown in FIG. 1. For convenience a heart wall may be referred to herein simply as a septum. It should be appreciated, however, that the structure and functions taught herein may be used to access regions other than a septum.

The guide 106 is adapted to carry (e.g., hold and/or direct the course of) an instrument 112 that creates a hole in the septum. For convenience, such an instrument may be referred to herein as a piercing instrument. It should be appreciated, however, that such an instrument may use techniques other than piercing to create a hole in a septum. For example, a piercing instrument may be adapted to drill or cut or use any other suitable technique to create a hole in or provide other similar access through the septum.

Once the guide 106 is in an engaged positioned (e.g., the distal end 108 is directed toward a particular location on the septum 110 as shown in FIG. 1), the piercing instrument 112 may be routed through the guide 106 such that a distal end 114 of the piercing instrument 112 is directed toward that same location. The piercing instrument 112 may then be pushed, turned, etc., to create a hole in the septum 110.

In some embodiments the piercing instrument 112 may function as a guidewire that facilitates delivering other components to the hole. For example, a guidewire-like instrument 112 may include a sharp distal end 114 and be adapted to temporarily maintain its position on the distal side of the septum (e.g., in the left atrium). Here, the instrument 112 may include an expandable locking mechanism on its distal end. Once the locking mechanism is positioned in the left atrium, the locking mechanism may be expanded to a size that is larger than the diameter of the hole (see, e.g., locking mechanism 130 in FIG. 2). This, in turn, prevents the distal end of the instrument 112 from being pulled out of the left atrium. Once the guide 106 is removed from the guidewire, one or more other components (e.g., a sheath) may then be routed over the instrument 112 to the hole to enable a lead or other device to be implanted in the septum. Thus, this is one way the delivery instrument 100 may be adapted to carry a lead to an implant site. To remove the instrument 112, the locking mechanism is reconfigured to its original orientation thereby permitting the distal portion of the instrument 112 to pass back through the hole. These and other related operations are discussed in more detail below.

Alternatively, a separate guidewire may be used with the delivery instrument 100. In some embodiments, after the piercing instrument 112 creates the hole, a guidewire (not shown) may be routed through a lumen in the piercing instrument 112 then through the hole. The piercing instrument 112 is then removed, leaving the guidewire in place. The guidewire may have at its distal end a pig-tail configuration or some other suitable structure designed to prevent inadvertent dislodgement from the left atrium. Alternatively, in some embodiments the piercing instrument 112 is removed from the guide 106 so that a guidewire may be routed through the guide 106 and through the hole in the septum.

In some embodiments the delivery instrument 100 may be adapted to carry a lead to the implant site. For example, the guide 106 also may be adapted to carry an implantable lead.

The delivery instrument 100 also includes an elongated structural member (hereafter referred to as "component 116") that facilitates positioning the guide 108. A distal portion of the component 116 is adapted to engage (e.g., rest upon or be embedded within) tissue associated with (e.g., adjacent to or within) the coronary sinus. For convenience, such an engagement may simply be referred to herein as engaging the coronary sinus. For example, in some embodiments the component 116 may include one or more structural members 118 (e.g., tines or other suitable structure) that extend from the component 116 and are adapted to engage tissue associated with the coronary sinus. For example, upon implant a member 118 may be positioned to rest upon or otherwise engage tissue 132 adjacent an orifice (the ostium 120) of the coronary sinus. Through the use of members 118, the distal portion of the component 116 may be maintained at a known position. For convenience, a structural member adapted to be seated against or otherwise interact with tissue may be referred to herein as a seating structure. In some embodiments a distal portion 122 of the component 116 may be adapted to enter the coronary sinus. This also may serve to maintain the distal portion of the component 116 at a known position.

Through the use of a positioning component such as component 116, the delivery instrument 100 may be adapted to readily create a hole at a desired location in the septum 100. For example, when the guide 106 is in an engaged position the distal end 108 may be adapted to be a specified distance from a distal portion of the positioning component 116 that is engaged in tissue associated with (e.g., adjacent to or within) the coronary sinus.

Figure 2:
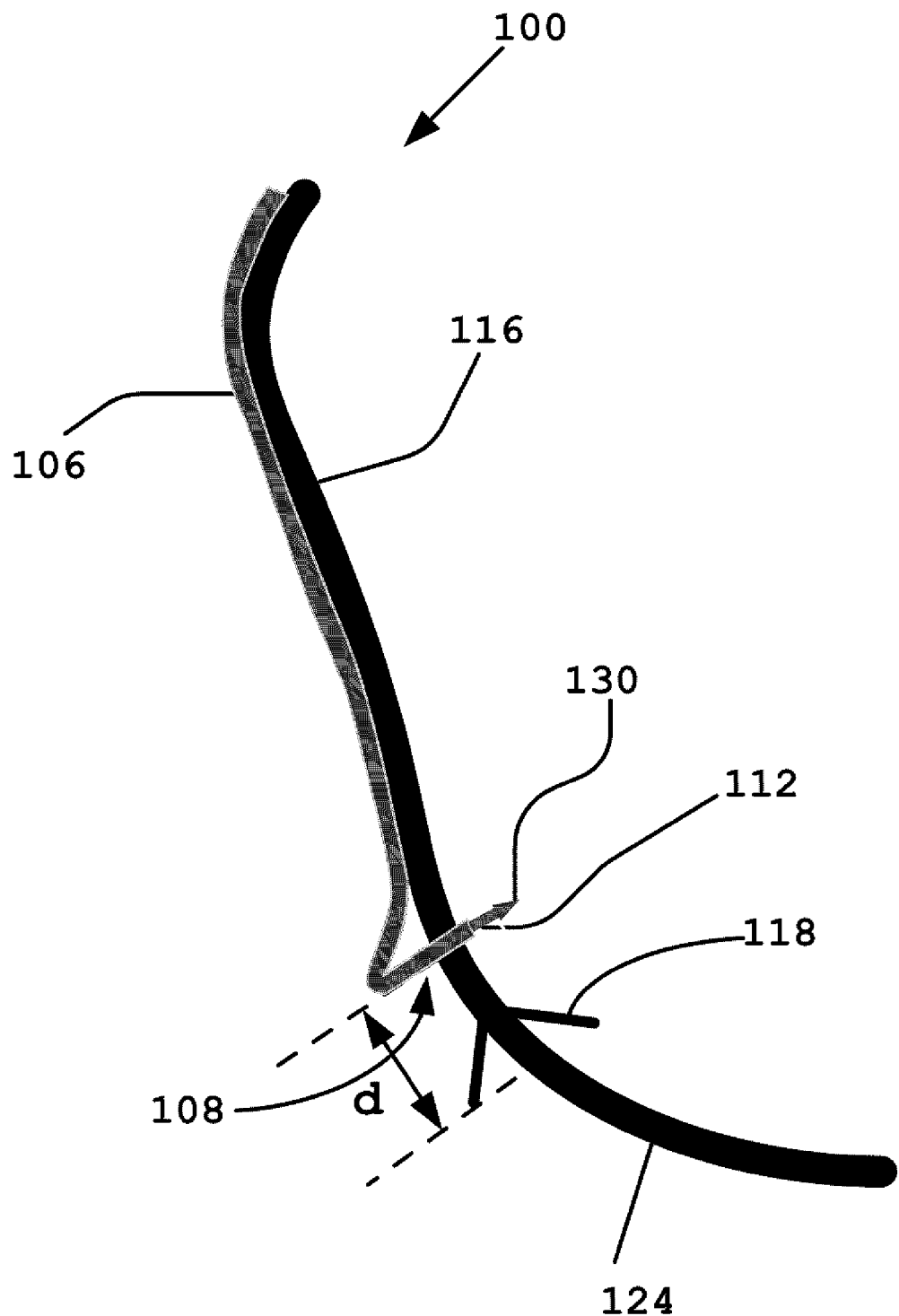
FIG. 2 is a simplified diagram of an embodiment of a delivery instrument.

FIG. 2 illustrates an example of such a distance relationship (for clarity, the heart H is omitted in FIG. 2). Here, the distal end 108 of the guide 106 is located a distance "d" from a portion (e.g., an end portion) of the tines 118 that may rest upon tissue adjacent the ostium of the coronary sinus. In some cases, the distance "d" may be measured from a hinge point of the tines 118 in the event the tines 118 will be pressed flat against the tissue. In some patients it may be desirable to define the puncture location at approximately 25 mm proximal to the level of the ostium of the coronary sinus in a plane perpendicular to the inter-atrial septum.

Advantageously, the delivery instrument may be adapted to provide ready (e.g., automatic) access to an area of the heart at or near the fossa ovalis. Here, the spatial relationship (e.g., distance and angle) between the coronary sinus and the fossa ovalis or the membranous part of the septum may be relatively consistent from patient to patient; particularly among those patients with a sick, and consequently enlarged, heart. For example, for many patients the distance "d" may be on the order of 2-3 cm. Thus, a delivery instrument may be provided for use with multiple patients with a single (or a few) predefined distance and angle relationship between these areas.

By adapting (e.g., sizing and spacing components of) the delivery instrument such that the distance "d" is properly specified, the piercing instrument 112 may be readily directed to a location in the inter-atrial septum at which it is desirable to create a hole. Consequently, a physician may readily gain access to the left atrium through the use of a familiar coronary sinus access procedure. That is, the physician positions the delivery instrument 100 at the coronary sinus in the same way the physician would position a sheath or other component during a typical coronary sinus lead implant procedure. Once the delivery instrument 100 is positioned in this manner, the guide 106 may automatically be in position to direct the piercing instrument 112 through the inter-atrial septum at the desired location. For example, referring again to FIG. 1 the delivery instrument may thus be adapted to create a hole in the fossa ovalis 126, a membranous portion of the septum 128, a muscular portion of the septum or some other location.

FIG. 2 also illustrates that the component 116 may include a distal portion 124 that is inserted into the coronary sinus. As discussed above, the portion 124 may help to securely position the delivery instrument 100 in the heart. In some embodiments the seating structure 118 may be positioned to ensure that only a specified length of the distal portion 124 of the delivery instrument 100 is placed into the coronary sinus.

In some embodiments the component 116 may comprise a catheter adapted to carry one or more leads or other components to the venous branches of the coronary sinus. For example, such a catheter may include a lumen for implanting a lead that is adapted (e.g., includes electrodes and coil at appropriate locations) to sense signals in and/or provide stimulation (e.g., pacing or shocking) signals to the left atrium and/or the left ventricle. Thus, the same delivery instrument 100 may be used for implanting leads or other components in both the coronary sinus and the left atrium. Consequently, additional flexibility may be provided for sensing and/or stimulating the left atrium, left ventricle other parts of the heart.

A delivery instrument as taught herein may thus provide an easy to obtain anatomical reference point for accessing the left side of the heart. In addition, the seating structure or other positioning techniques may provide an effective leverage point for the delivery instrument. Such a leverage point may prove useful when applying pressure at a proximal end of the delivery instrument to reorient the guide and/or create the hole in the septum.

Figure 3:
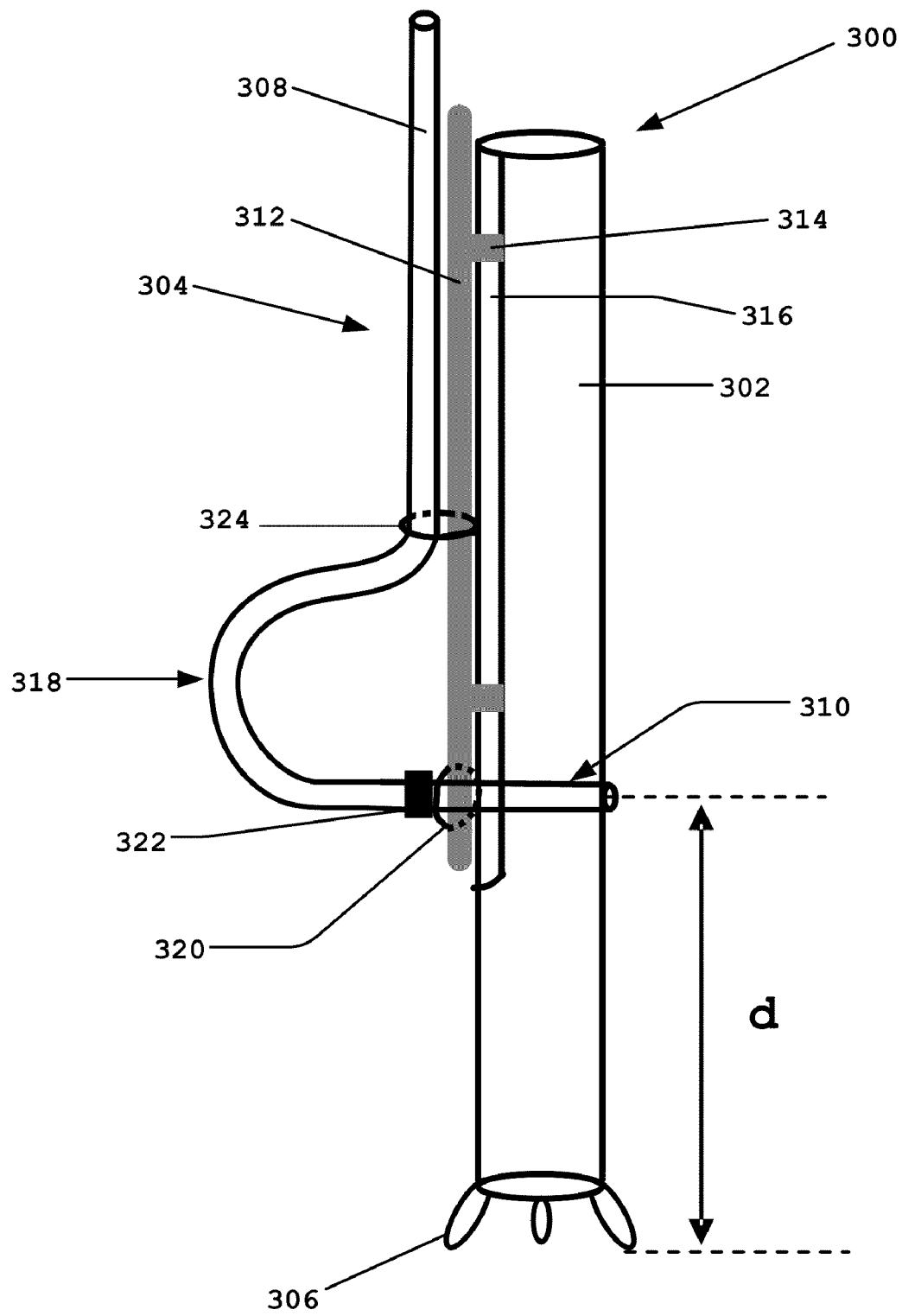
FIG. 3 is a simplified diagram of an embodiment of a delivery instrument in an engaged orientation.

Referring now to FIG. 3, various examples of components of a delivery instrument 300 will be discussed. For convenience only the distal portion of the delivery instrument 300 is shown. Accordingly, it should be understood that several of the components (e.g., components 302, 308 and 312) extend to a proximal end of the delivery instrument.

This embodiment of a delivery instrument includes a main catheter 302 (e.g., an elongated structural member that may be somewhat similar to the component 116) and a guide 304. In some embodiments the main catheter 302 is adapted to carry at least one lead (not shown) adapted for implant in the coronary sinus as discussed above. The example of FIG. 3 also shows that in some embodiments the seating structure (e.g., tines 306) may be connected to or extend from a distal end of the main catheter 302.

The guide 304 in this example includes a sealed track 308 that is adapted to carry (e.g., within a lumen) one or more of a piercing instrument, a guidewire, and a lead (not shown in FIG. 3). For example, a piercing instrument/guidewire may be inserted into a proximal end of the sealed track 308 and routed through the sealed track 308 until the distal end of the piercing instrument/guidewire exits the distal end of the sealed track 308. In some embodiments the sealed track may take the form of a catheter. Accordingly, for convenience, the sealed track may be referred to as a "guide catheter."

Figure 4:
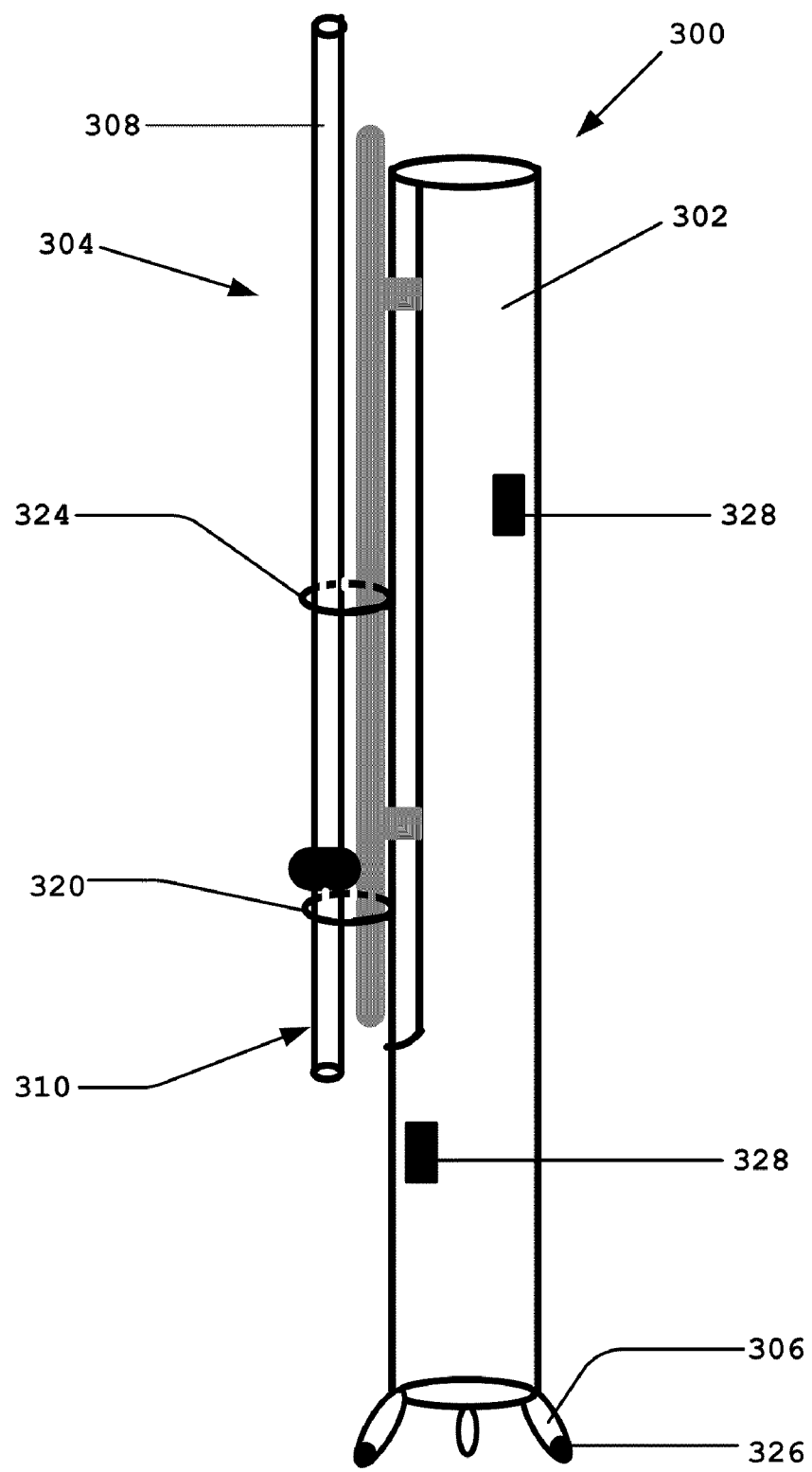
FIG. 4 is a simplified diagram of an embodiment of the delivery instrument of FIG. 3 in a retracted orientation.

The guide 304 is adapted such that the guide catheter 308 may be reoriented between the positions shown in FIGS. 3 and 4. Thus, when the delivery instrument 300 is routed through the venous system distal portions 310 and 318 of the guide catheter 308 may be oriented to lie substantially parallel to a longitudinal axis of the main catheter 302 as shown in FIG. 4. Then, once the distal portion of the delivery instrument 300 has been co-located with the coronary sinus, the distal portion 310 of the guide catheter 308 may be oriented at an angle to the longitudinal axis of the main catheter 302 as shown in FIG. 3. The selected angle may depend on the requirements of a given case. In some cases the distal portion 310 may be reoriented to be substantially perpendicular to the longitudinal axis of the main catheter 302. Other cases may use a smaller or larger angle.

FIG. 3 illustrates one example of how the guide 304 may be coupled with the main catheter 302. It should be appreciated that a variety of other fixation mechanisms may be used to couple or otherwise join these components or any similar components discussed herein. Alternatively, in some embodiments, the guide 304 and main catheter 302 may comprise an integrated component.

In FIG. 3 the guide catheter 308 is coupled to an attachment member 312 of the guide 304. The member 312 is adapted to facilitate reorientation of the guide catheter 308 and coupling of the guide 304 with the main catheter 302. Here, the member 312 may include one or more fixtures 314 that fasten the member 312 to the main catheter 302.

In some embodiments the guide 304 is releasably coupled to the main catheter 302. For example, the fixtures 314 may slide within a track 316 of the main catheter 302 or be mounted in some other manner that facilitates separation of the guide 304 from the main catheter 302. In this way, the guide 302 may be released from the main catheter 302 in the event this is desirable at some point in time during the implant procedure.

Similarly, in some embodiments the member 312 may be repositionable on the main catheter 302. In this way, the distance "d" between the distal portion 310 and the seating structure 306 may be adjusted as necessary. Various mechanisms may be used to provide such repositioning. For example, a mechanism may provide several fixed positions or a range of positions. In addition, such a mechanism may employ fasteners or any other suitable coupling mechanism.

The member 312 also includes several components that facilitate reorienting the guide catheter 308. A coupler 324 slideably carries the guide catheter 308. That is, the guide catheter 308 is free to slide within the coupler 324 in either a distal or a proximal direction.

The member 312 and/or the guide catheter 308 also may include a mechanism to restrain sliding of a distal portion of the guide catheter 308 relative to the member 312. In this way, the guide catheter 308 is forced to reorient when the guide catheter 308 is pushed in a distal direction. For example, a portion 318 of the guide catheter 308 may bend outwardly when a physician pushes the proximal end of the guide catheter 308 in a distal direction. Here, the portion 318 may be predisposed to bend in a given direction (e.g., outward). In an alternative embodiment discussed below, reorientation is achieved by sliding a member (somewhat similar to member 312) in a proximal direction with the guide catheter 308 (or similar structure) held steady.

In the example of FIG. 3, a coupler 320 serves to carry and hold the distal portion 310. For example, the coupler 320 prevents the distal portion of the guide catheter from moving in a distal direction further beyond the coupler 320. In the example of FIG. 3, the guide catheter 308 may include a stop 322 or the member 312 and the guide catheter 308 may include a fixation mechanism 322 to prevent the guide catheter 308 from moving further past the coupler 320.

The coupler 320 may be further adapted to facilitate reorientation of the distal portion 310. For example, as shown in FIGS. 3 and 4, the coupler 320 may reorient (e.g., bend) as the distal portion 310 reorients.

FIG. 4 illustrates that the delivery instrument 300 may incorporate one or more imaging markers 326 and 328 (e.g., made of radio-opaque material). These markers may be used in conjunction with imaging equipment to verify the location of and/or aid in the positioning of the delivery instrument 300. Such imaging equipment may utilize, for example, x-ray, fluoroscopy or any other suitable imaging technique.

In some embodiments, one or more markers may be employed on a distal portion of the main catheter 302 to verify that a distal portion of the delivery instrument is co-located with (e.g., resting on or positioned next to) tissue associated with the coronary sinus. For example, in some embodiments one or more markers 326 may be mounted on or incorporated into one or more of the tines 306. In some embodiments the position of the delivery instrument is determined by lining up the ostium of the coronary sinus with one or more markers (not shown) mounted on or incorporated into a distal portion of the main catheter 302. Such a configuration may be used instead of or in addition to other positioning techniques (e.g., as discussed herein).

In some embodiments, one or more markers may be employed on a distal portion of the delivery instrument 300 to determine the rotational orientation (i.e., about the longitudinal axis) of the delivery instrument 300. For example, markers 328 of various shapes and locations (or one marker) may be mounted on or incorporated into the main catheter 302 and/or the guide 304. The relative positions of the markers 328 as detected by imaging equipment may provide an indication as to the rotational orientation of the delivery instrument 300. In this way, the attending physician may determine whether the delivery instrument 300 needs to be rotated to ensure that the distal portion 310 of the guide catheter 308 is directed toward the septum or other desired location. For example, when a patient is lying on his or her back, the distal portion 310 may be directed generally downward (toward the posterior of the heart) to pierce the fossa ovalis.

Figure 5:
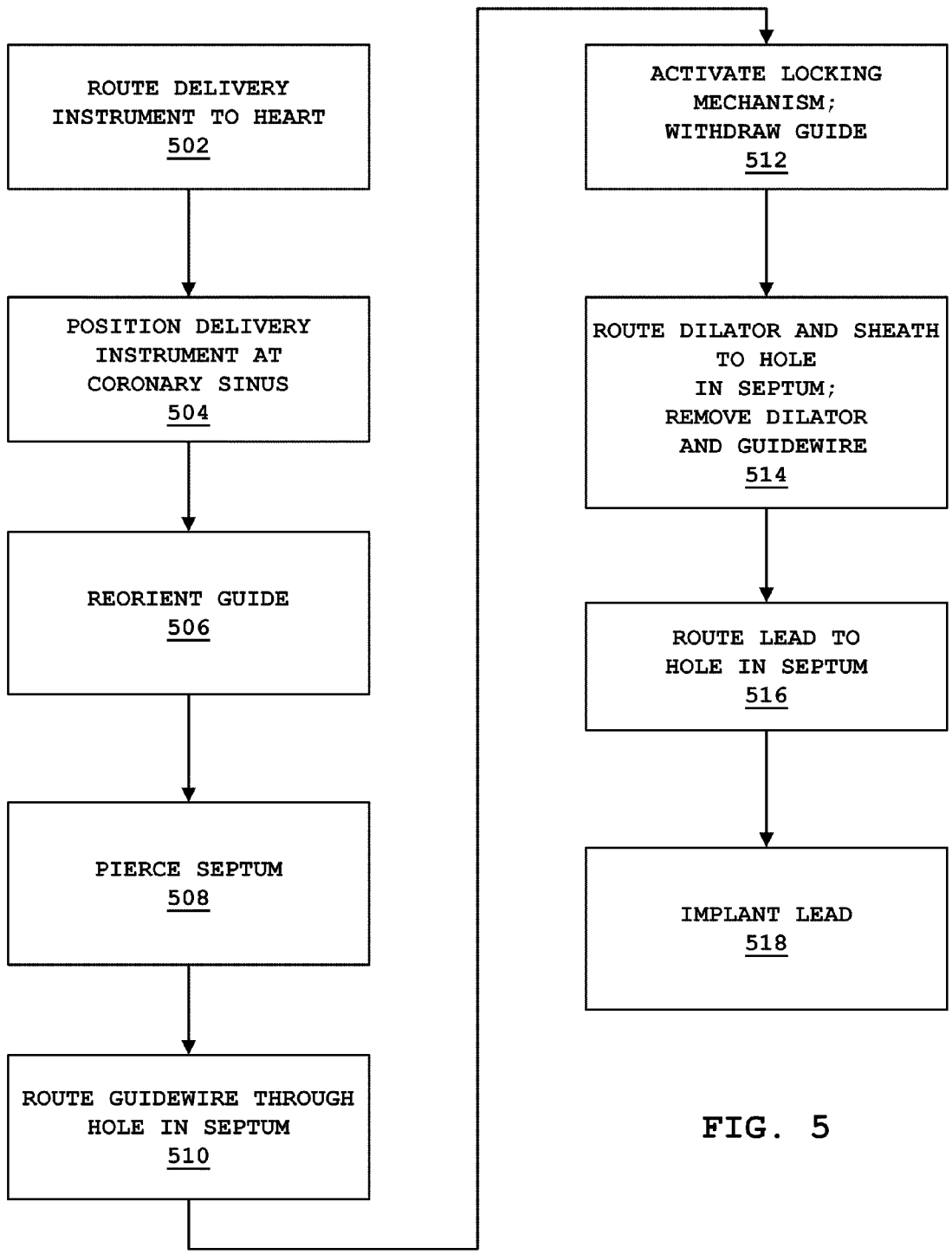
FIG. 5 is a flow chart of an embodiment of operations that may be performed to implant a lead or a device in a patient.

With the above description in mind, additional details of a transseptal implant procedure will now be discussed in conjunction with FIGS. 5-11. FIG. 5 is a flowchart illustrating selected implant operations. FIGS. 6-11 illustrate examples of how the delivery instrument and other components may be routed into and/or positioned in the heart.

Figure 6:
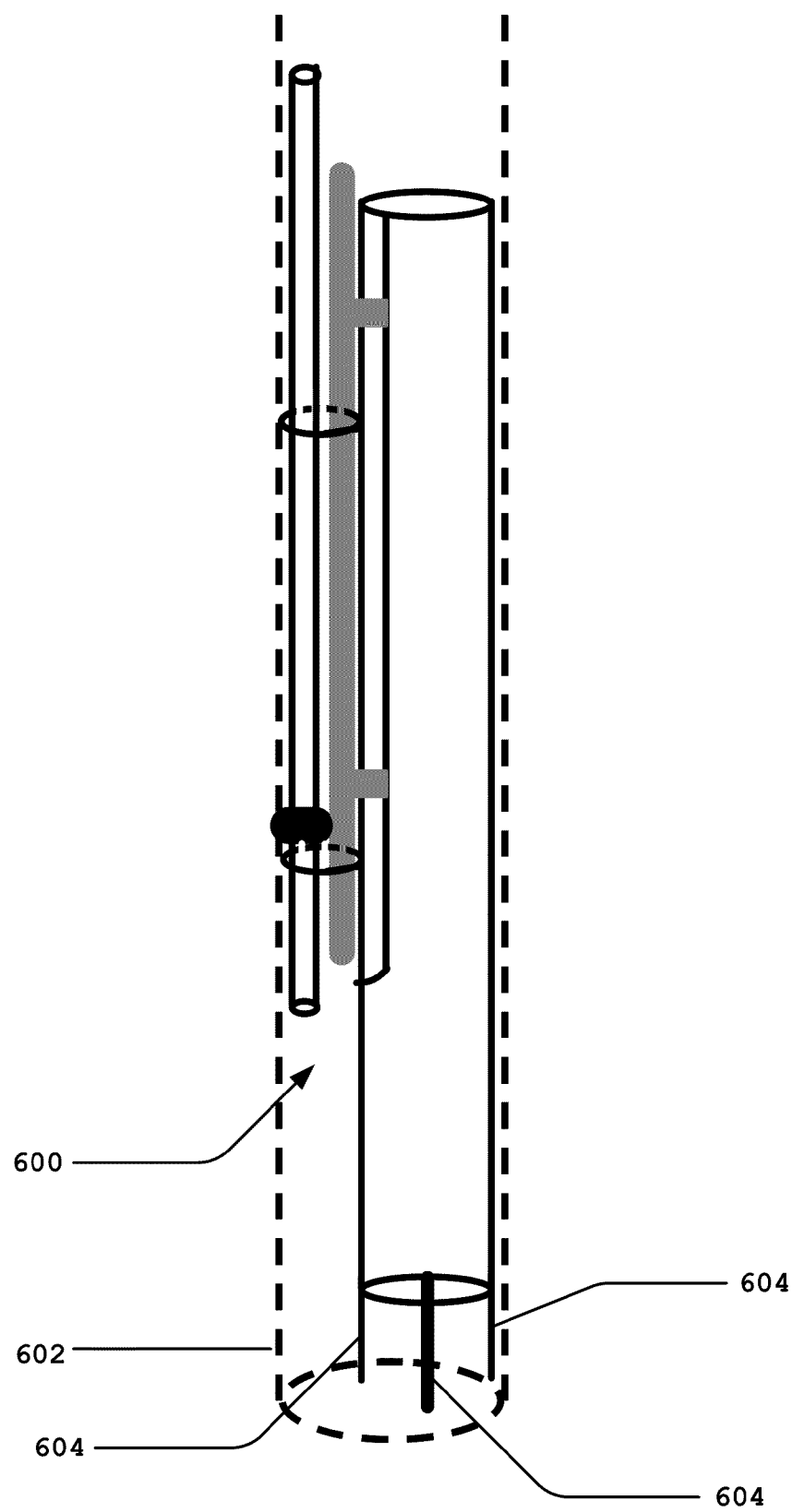
FIG. 6 is a simplified diagram of an embodiment of the delivery instrument of FIG. 4 carried within a delivery sheath.

Referring now to FIG. 5, as represented by block 502 the delivery instrument is initially routed to the heart via a superior transvenous technique. Thus, a distal portion of the delivery instrument may initially be inserted into a vein above the heart and routed through the venous system into the heart As illustrated in FIG. 6, a delivery instrument 600 may be placed in a sheath 602 prior to implant to facilitate routing the delivery instrument 600 through the venous system. For convenience, the sheath 602 is depicted in phantom to more easily show the components of the delivery instrument 600 within the sheath 602. Here, it may be seen that the seating structure 604 (e.g., tines) may be adapted to orient to a position that is substantially parallel to a longitudinal axis of the delivery instrument 600. Alternatively, in other embodiments the seating structure may be retractable (e.g., using a stylet) whereby the seating structure is drawn into the distal portion of the delivery instrument during delivery (not shown).

Once the distal portion of the delivery instrument 600 reaches the interior of the heart, the seating structure 604 may be allowed to reorient to an extended orientation. For example, in embodiments that use the sheath 602, the sheath 602 may be withdrawn from the delivery instrument 600. The seating structure 604 may then automatically (e.g., by spring or memory action) expand from the delivery instrument (e.g., as shown in FIG. 4). In embodiments that use a retractable seating structure, the seating structure may be extended out of the delivery instrument at this time.

As represented by block 504, the delivery instrument is co-located with the coronary sinus. As discussed above, in some embodiments this may involve positioning a distal portion (e.g., a seating structure such as tines) of the delivery instrument against tissue associated with the coronary sinus as shown in FIG. 1. In some embodiments this may involve using imaging (e.g., of the coronary sinus and markers on the delivery instrument) to verify whether a distal portion of the delivery instrument is at a desired position relative to the coronary sinus.

At block 506, the guide on the delivery instrument is reoriented such that the distal end of the guide is directed toward the septum (e.g., as shown in FIGS. 1 and 3). As discussed herein, this may be accomplished in some embodiments by pushing or pulling on one or more sytlets that extend from a proximal end of the delivery instrument to the guide and/or associated components at the distal end of the delivery instrument.

Figure 7:
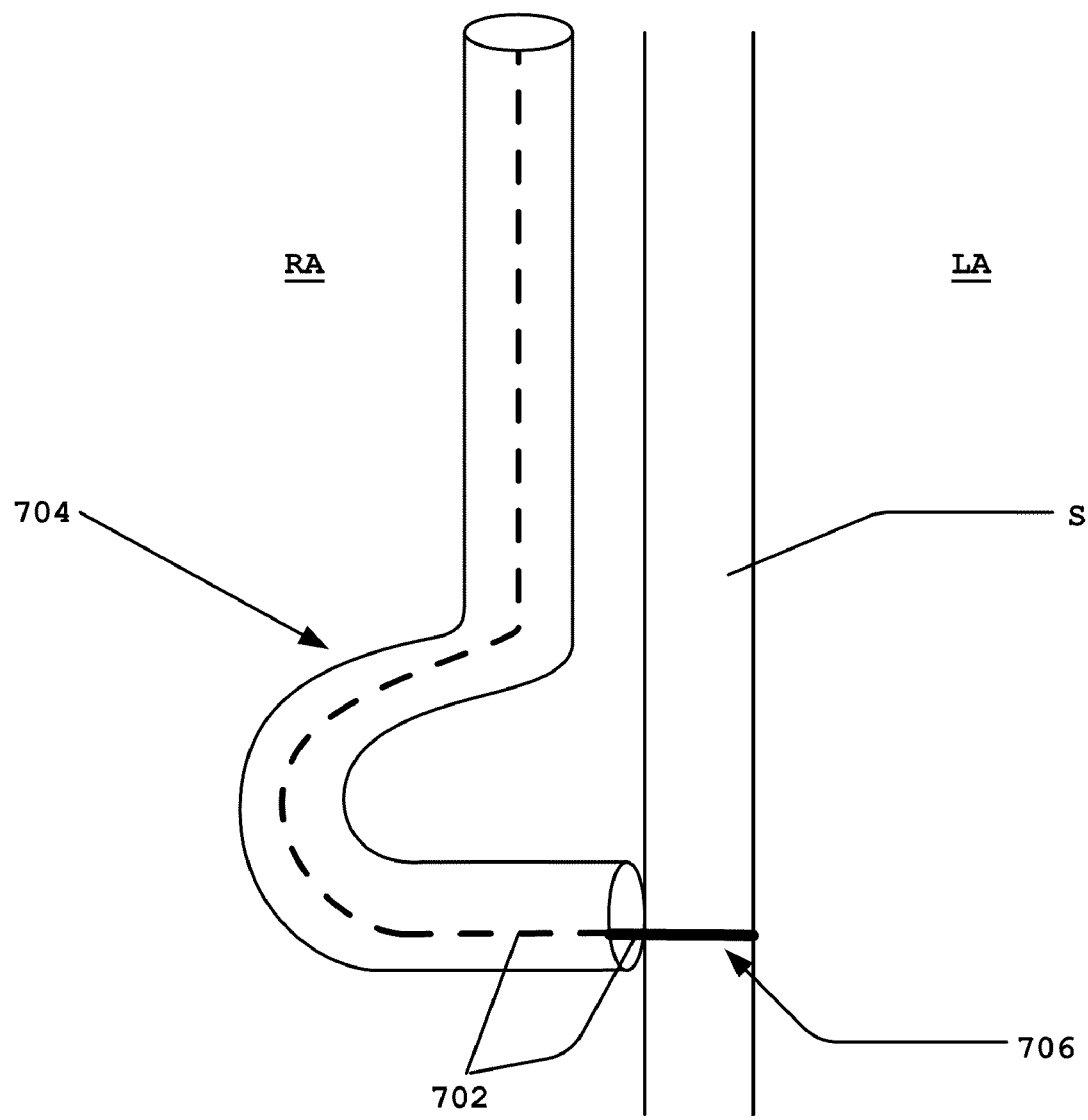
FIG. 7 is a simplified diagram of an embodiment of a guidewire-like piercing instrument routed through a delivery instrument.

As represented by block 508, the guide is then used to pierce the septum. For example, as shown in FIG. 7 a piercing instrument 702 is routed through a guide 704 (shown in a simplified form) placed in the right atrium ("RA") and forced through the septum S to create a hole 706 through the septum S to the left atrium ("LA").

Figure 8:
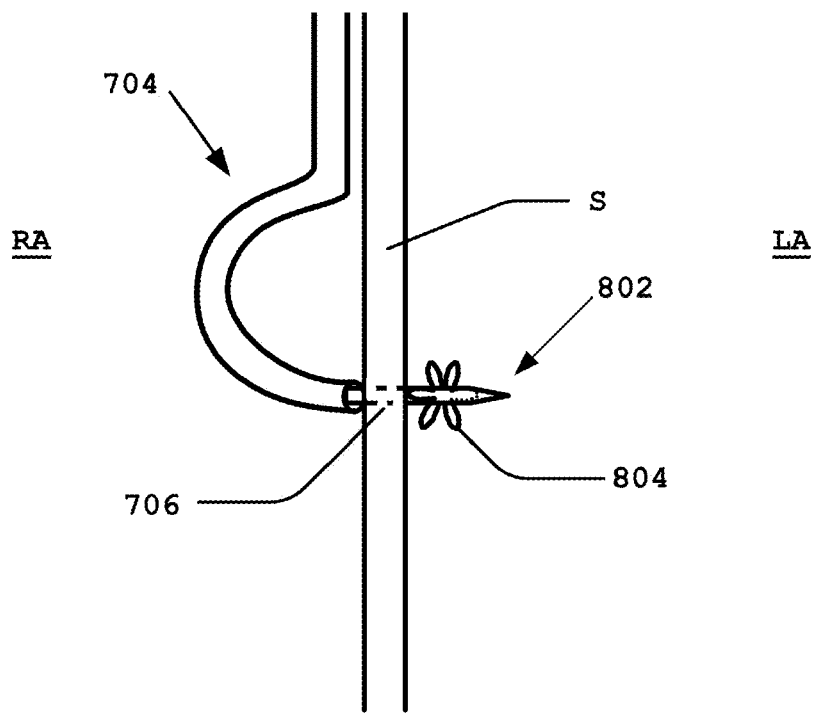
FIG. 8 is a simplified diagram of an embodiment of a distal locking mechanism of a guidewire-like piercing instrument.

Next, at block 510, a guidewire (e.g., a guidewire-like piercing instrument or other suitable component) 802 is routed through the hole 706 in the septum S (FIG. 8). A distal portion of the guidewire 802 will thus be positioned in the left atrium as illustrated in FIG. 8.

A locking mechanism 804 may then be deployed to temporarily prevent the distal portion of the guidewire 802 from being pulled out of the left atrium (block 512). Various mechanisms may be used for this purpose. For example, in some embodiments a locking mechanism may comprise a braided wire portion of a guidewire wherein the braided portion expands in a radial manner into a set of overlapping loops (e.g., to form a small umbrella-like structure) upon deployment of the locking mechanism. Here, the locking mechanism may be deployed by sliding a stylet in the guidewire. In other embodiments the locking mechanism may take the form of a pig-tail-like curl or some other suitable form. Several examples of locking structures are described in U.S. Patent Application Publication No. 2006/0196137, filed Feb. 23, 2006, the disclosure of which is hereby incorporated by reference herein.

Figure 9:
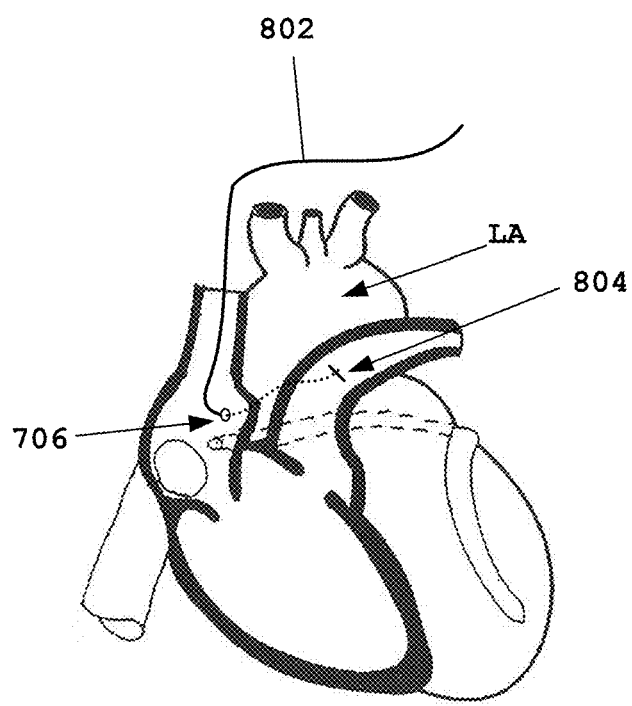
FIG. 9 is a simplified diagram of an embodiment of a guidewire-like piercing instrument implanted in a heart.

Once the locking mechanism 804 has been deployed, the guide may be removed from the guidewire (e.g., as depicted in FIG. 9). In some embodiments this may involve withdrawing the entire delivery instrument from the heart leaving only the guidewire in place. In other embodiments only certain components may be withdrawn at this point. For example, in embodiments where the delivery instrument includes a catheter for implanting a coronary sinus lead, it may be desirable to leave the coronary sinus catheter in the heart at this point of the procedure. Consequently, as discussed herein, the delivery instrument may be adapted such that one or more components are releasably attached to another component. For example, in some embodiments the guide may be released from the coronary sinus catheter. In this case, only the guide may be withdrawn from the heart. In some embodiments a guide catheter may be releasably attached to the guide. Thus, in this case, only the guide catheter may be withdrawn.

Figure 10:
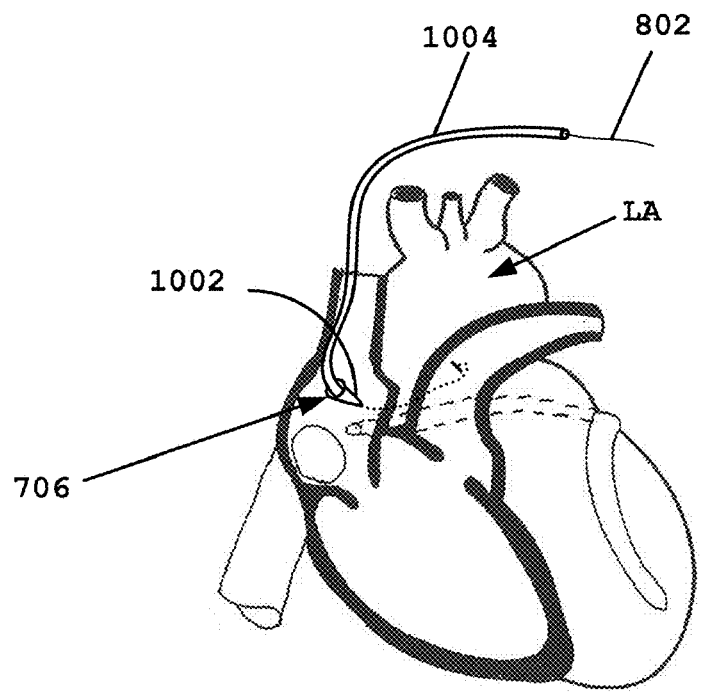
FIG. 10 is a simplified diagram of an embodiment of a sheath and dilator routed over a guidewire.

As represented by block 514 and illustrated in FIG. 10, a dilator 1002 and a sheath 1004 are routed over the guidewire 802. The dilator 1002 is forced into the hole 706 to widen the hole 706 so that the sheath 1004 may be routed through the hole 706. After the sheath 1004 is inserted into the hole 706, the dilator 1002 and the guidewire 802 may be withdrawn.

Figure 11:
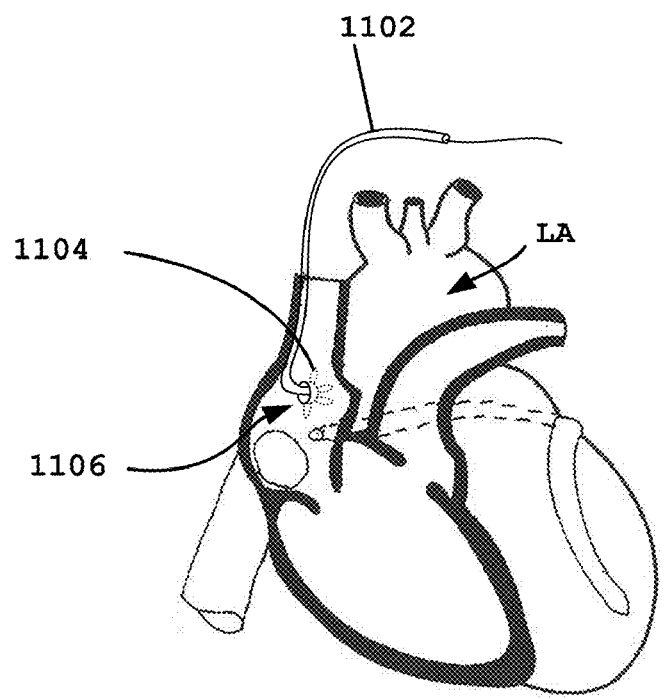
FIG. 11 is a simplified diagram of an embodiment of a lead implanted in a heart.

As represented by block 516 and illustrated in FIG. 11, a lead 1102 may then be routed through the sheath to implant the distal end of the lead 1102 into or through the hole in the septum. Here, one or more attachment mechanisms (e.g., tines) 1104 may be employed to secure the distal end of the lead (or an associated device) to the septum (block 518).

The lead 1102 may include one or more devices for sensing conditions in or providing therapy to the left atrium. For example, a pressure sensor 1106 may be located at the distal end of the lead 1002. The pressure sensor 1106 may thus be positioned on the left side of the heart (or be coupled to a pressure wave carrying channel exposed to the left side of the heart) to obtain pressure readings from the left side of the heart. It should be appreciated that the lead may incorporate other devices (e.g., electrodes) for sensing or providing treatment.

Figure 12:
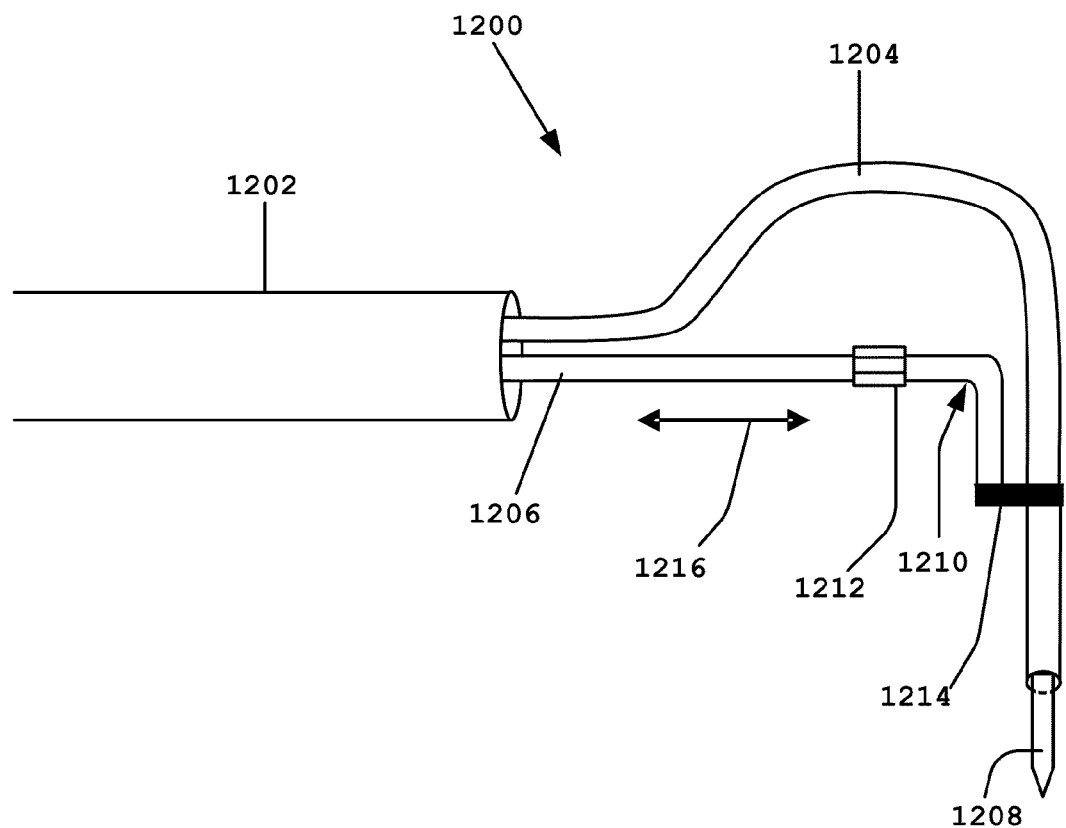
FIG. 12 is a simplified diagram of an embodiment of a guide of a delivery instrument that directs a piercing instrument toward a septal wall of a heart.
Figure 13:
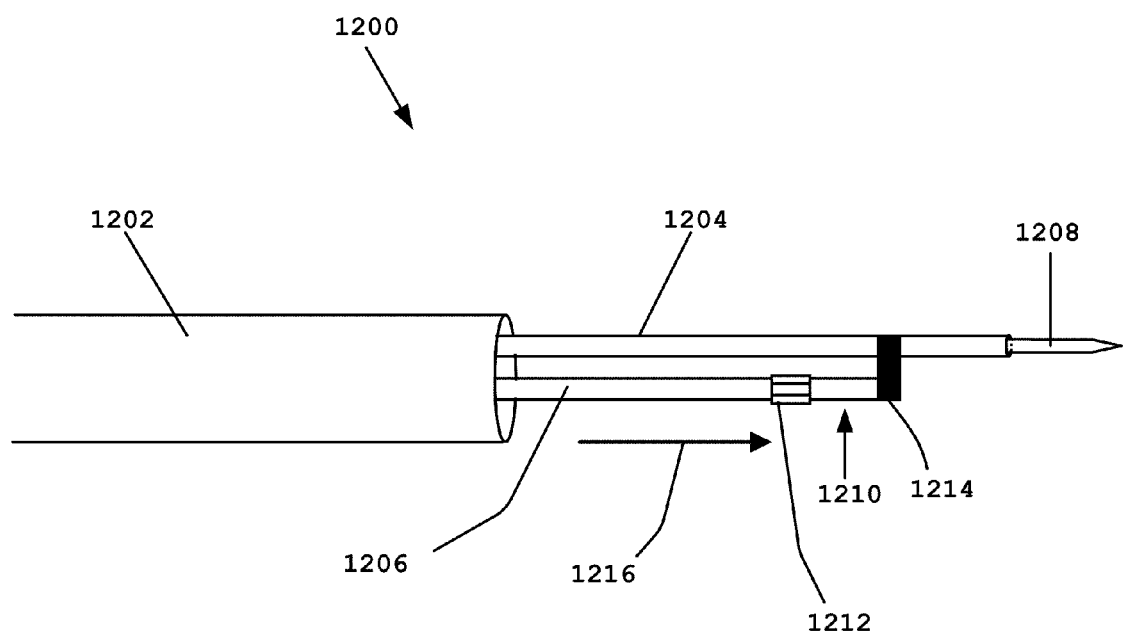
FIG. 13 is a simplified diagram of an embodiment of the guide of FIG. 12 in a retracted orientation.

Referring now to FIGS. 12 and 13, various details of an embodiment of a guide 1200 will be discussed. The guide 1200 includes a catheter 1202 adapted to carry a guide catheter 1204 and a flexible, elongated member 1206 (e.g., a wire, a stylet, etc.). The guide catheter 1204 is adapted to slideably carry a piercing instrument and/or a guidewire 1208 as discussed herein.

As represented by the arrows 1216, one or both of the guide catheter 1204 and the elongated member 1206 may slide within the catheter 1202. In this way, the guide 1200 may be reoriented between a retracted position (FIG. 13) and an engaged position (FIG. 12). The arrow 1216 in FIG. 13 illustrates an embodiment where a sliding movement of the elongated member 1206 in a distal direction (to the right in FIG. 13) causes the guide catheter 1204 to straighten.

The guide catheter 1204 is coupled with the elongated member 1206 via a flexible coupling mechanism 1210 and associated fixtures 1212 and 1214. Here, the operation of the coupling mechanism 1210 facilitates reorientation of the guide catheter 1204. Specifically, as the guide catheter 1204 is moved to the right (or the elongated member 1206 is moved to the left), the coupling mechanism bends to facilitate reorientation of the guide catheter 1204 to an orientation with a sharp out-of-plane turn as illustrated in FIG. 12.

The coupling mechanism 1210 may take various forms. In the example of FIGS. 12 and 13, the coupling mechanism 1210 comprises a pair of flexible wires that are fixed to the guide catheter 1204 and the elongated member 1206 by suitable fixtures 1214 and 1212, respectively. It should be appreciated based on the teachings herein that other suitable coupling mechanisms may be incorporated into a delivery instrument.

Figure 14:
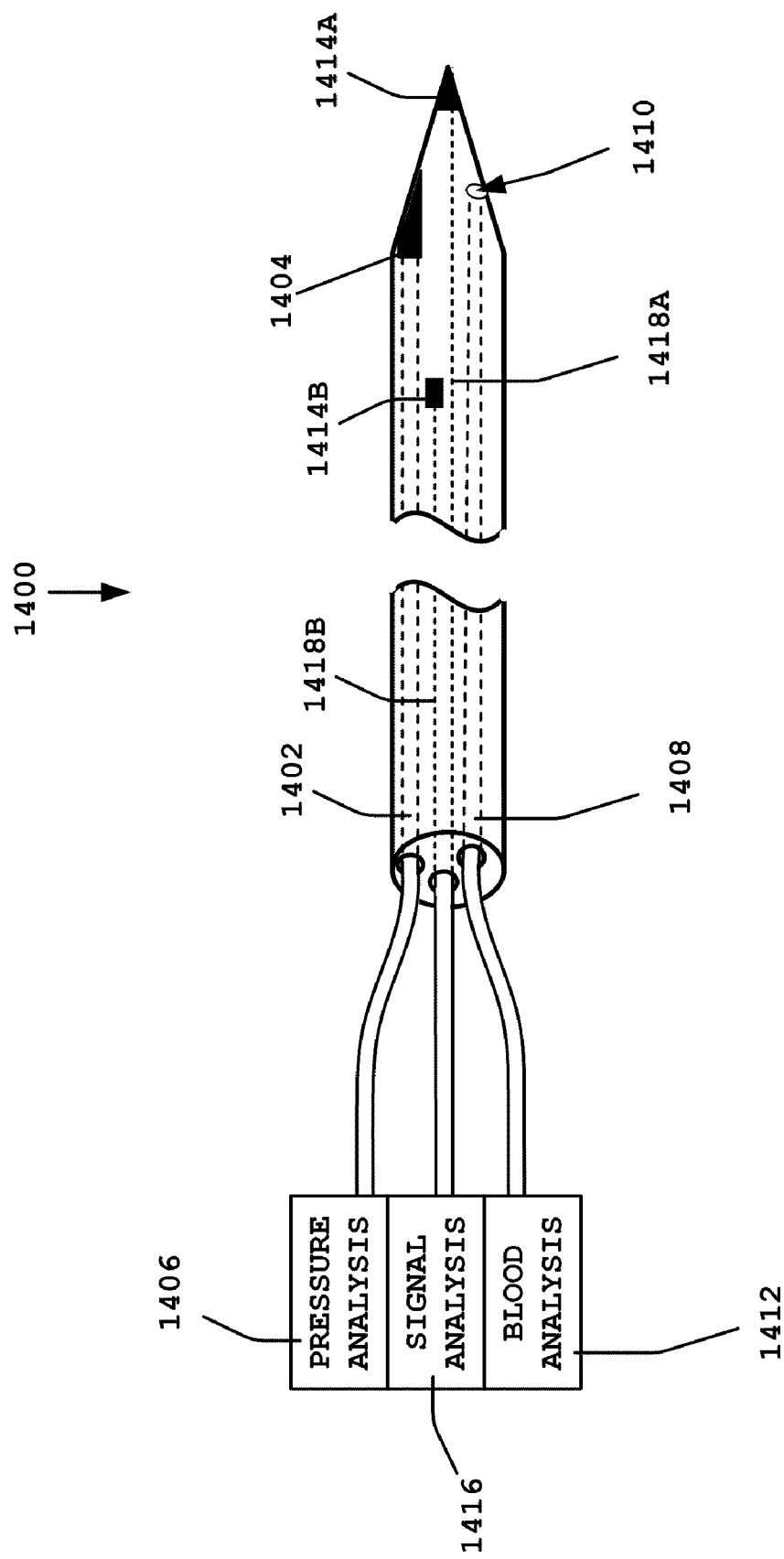
FIG. 14 is a simplified diagram of an embodiment of a guidewire.

Referring now to FIG. 14, in some embodiments a guidewire (e.g., the guidewire-like piercing instrument) 1400 may include one or more lumens. For example, in some embodiments the guidewire 1400 may have an internal lumen 1402 that is used to record pressure waveforms. Here, the lumen 1402 may transfer pressure waves to a pressure analysis component 1406. Alternatively, the lumen 1402 may include a pressure sensor 1404 that sends pressure reading signals to a pressure analysis component 1406. In some embodiments the guidewire 1400 may have an internal lumen 1408 with a port 1410 that is used to aspirate blood that is sent to a blood analysis component 1412. The data collected by either of these techniques may be beneficial for confirming entry into the desired cardiac chamber. For convenience the guidewire 1400 is depicted in FIG. 14 with multiple lumens. In practice, however, a guidewire may incorporate a different number of lumens (e.g., typically one). The piercing instrument 1400 also may include electrodes 1414A and 1414B that are coupled, via conductors 1418A and 1418B, to an electrical signal analysis component 1416 that measures electrical activity. In this case, the encountered electrical measurements may be used to further verify and pinpoint the location where the puncture across the septum will be performed.

In some embodiments a piercing instrument/guidewire may be used to partially puncture the right side of the septum wherein the locking mechanism is activated prior to performing the puncture. When a partial puncture is performed into the septum, the piercing instrument may be used to evaluate electrical pacing and sensing performance at the puncture site. If the sensed electrical performance proves to be adequate, a full puncture may then be performed. If the sensed electrical performance is inadequate, then the puncture site may be modified by adjusting the distance "d" or a decision may be made to abort the procedure.

A variety of structures may be employed to securely hold an implantable lead in place and to direct a piercing instrument to a desired location in the heart. Additional examples of such structures will now be discussed in conjunction with FIGS. 15, 16 and 17.

FIG. 15 illustrates an embodiment of a delivery instrument 1500 that includes a catheter 1504 (e.g., a delivery tube) and a guide structure 1506 (a portion of which is depicted as being shaded) that are adapted to slide longitudinally with respect to one another and within a main catheter 1502. All of the components associated with the catheter 1504 and the guide structure 1506 shown in FIG. 15 are adapted to (e.g., are sufficiently flexible) to enable these components to be collapsed as necessary to slide within the main catheter 1502. FIG. 15 illustrates a condition where the components have been pushed out of a distal end of the catheter 1502.

Figure 15A:
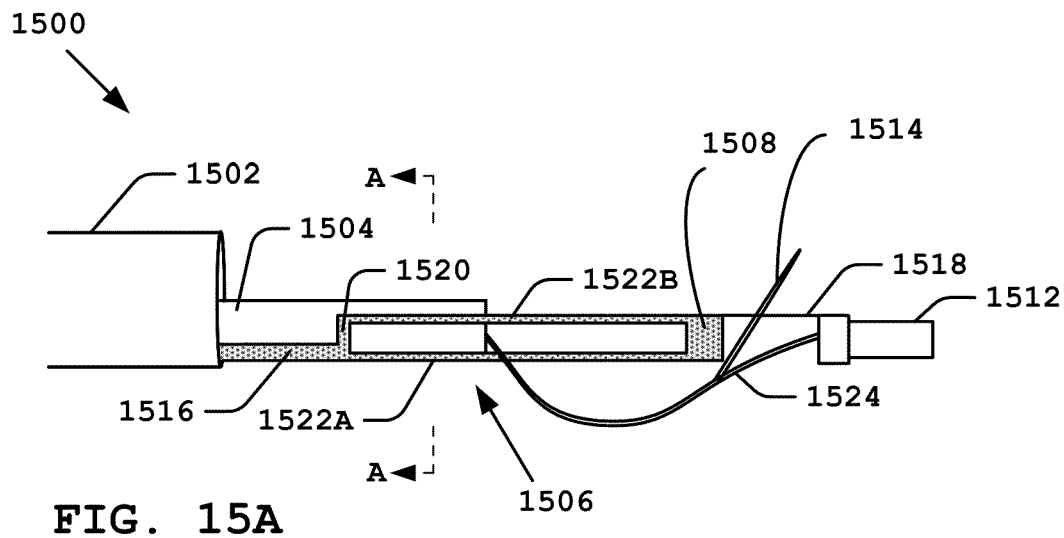
FIGS. 15A, 15B and 15C, is a simplified diagram of an embodiment of a delivery instrument.
Figure 15B:
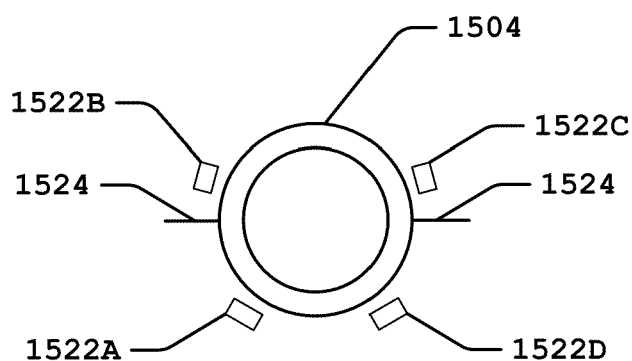
Figure 15C:
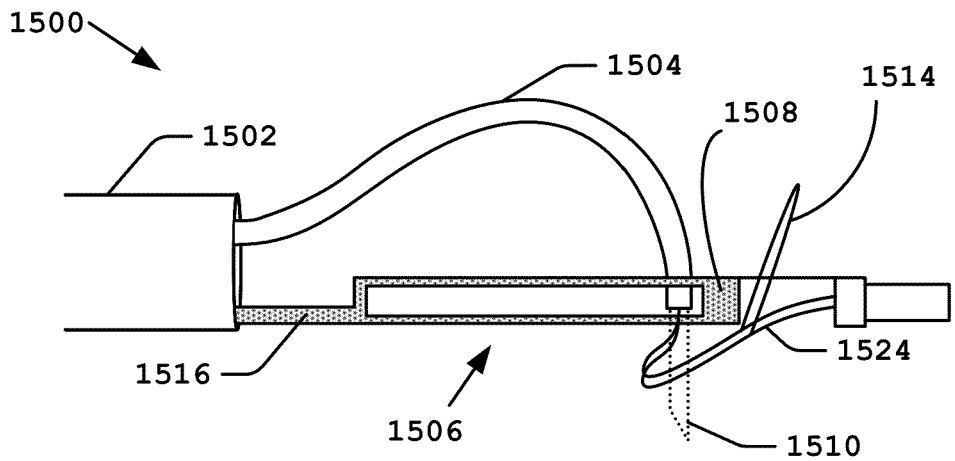

When the catheter 1504 is pushed in a distal direction relative to the guide structure 1506, engagement of a distal portion of the catheter 1504 with a portion 1508 of the guide structure 1506 causes the catheter 1504 to deflect as shown in FIG. 15C. Consequently, the delivery instrument 1500 may facilitate delivery of a piercing instrument 1510 through the catheter 1504 at an angle that enables direct access to a heart wall (e.g., the septum between the left and right atria).

The guide structure 1506 includes a structural member 1512 (e.g. a tube-like component) at its distal end that may be adapted to partially enter the coronary sinus and also includes a flexible structural member 1514 (e.g., a wire-like component) that may be adapted to engage tissue adjacent the ostium of the coronary sinus. Through the use of the components 1512 and 1514, the distal end of the delivery instrument 1500 may be seated within and against the coronary sinus to secure the delivery instrument 1500 in place and add support for deflecting the catheter 1504 and forcing the piercing instrument 1510 through the septal wall.

Several of the components of the guide structure 1506 will now be treated in more detail. A proximal link member 1516 extends through the main catheter 1502 to the proximal end of the main catheter 1502 to enable the guide structure 1506 to be independently slid with respect to the main catheter 1502 and the catheter 1504. A linking member 1518 attaches the structural member 1512 with the main (shaded) portion of the guide structure 1506.

The main portion of the guide structure 1506 may be U-shaped, for example, open at the top as viewed in FIG. 15. The structure 1508 may comprise a tube-like structure within which the distal end of the catheter 1504 may enter. The portion of the structure 1506 between upright elements 1508 and 1520 may comprise four strips 1522A-D that form an angular array around the catheter 1504. The annular array is depicted, in part, in FIG. 15B which illustrates the catheter 1504 and the guide structure 1506 as seen from view A-A in FIG. 15A. In this view, the upright elements 1508 and 1520 that support the strips 1522A-D are not present. FIG. 15B illustrates that the shape of the guide structure 1506 restricts the bending of the catheter 1504 (as shown in FIG. 15C) to an upward direction, as viewed from the perspective of FIG. 15.

A flexible structural member 1524 (e.g., a wire-like structure) serves to further hold the catheter 1504 relative to the guide structure 1506. The structure 1524 essentially comprises a flexible loop having an apex at a distal end of the catheter 1504 and an apex at a proximal wall of the structure 1512. As shown in FIG. 15B, the arms of the structure 1524 extend outward from the catheter 1504 and between either the strips 1522A and B or the strips 1522C and D. From FIGS. 15A and C it may be seen that the structure 1524 allows the catheter 1504 to slide relative to the guide structure 1506, yet prevents the distal portion of the catheter 1504 from completely exiting the guide structure 1506.

The structure 1514 extends from the structure 1524 to form a partial loop that extends over the guide structure 1506. In examples of FIGS. 15 A and 15C, the loop is depicted as extending over the member 1518. Thus, it should be appreciated that the loop formed by the structure 1514 may be manipulated to reorient from a relatively flat orientation (longitudinal with the axis of the main catheter 1502) upon delivery through a vein to a relatively perpendicular orientation upon implant. In the latter case, the structure 1514 may, for example, provide a seating structure for engaging tissue such as the tissue surrounding the ostium of the coronary sinus as discussed herein.

Figure 16:
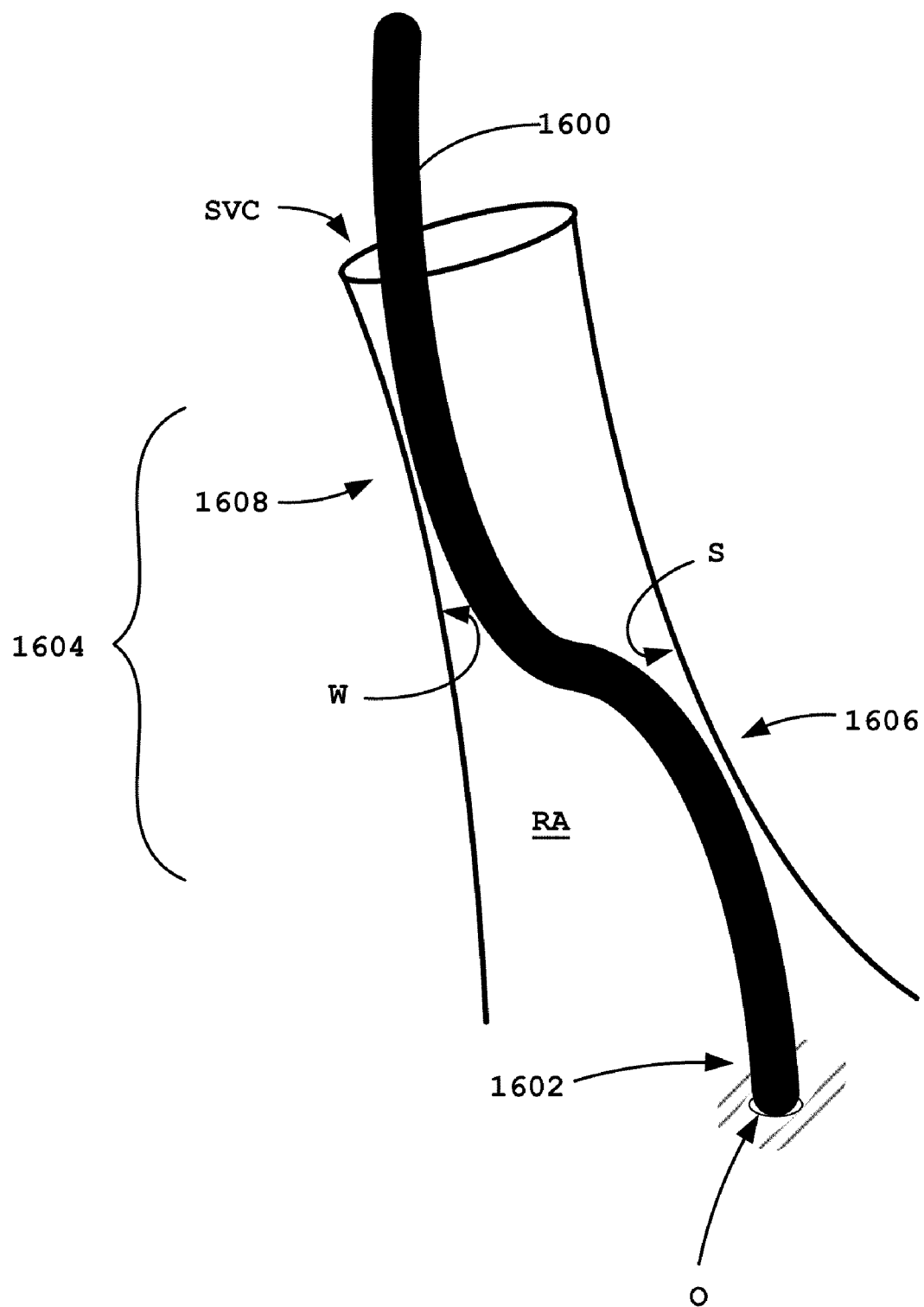
FIG. 16 is a simplified diagram illustrating an embodiment of a delivery instrument having a curved shape to facilitate secure placement of the delivery instrument.

FIG. 16 illustrates, in a simplified manner, an embodiment of a distal portion of a body 1600 of a delivery instrument implanted in patient's heart. As discussed above, a distal end 1602 of the instrument body 1600 may engage the ostium O of the coronary sinus.

The body 1600 is formed with a resilient curved portion 1604. The instrument body 1600 is constructed of a sufficiently flexible material such that the curved portion 1604 may be straightened as necessary (e.g., using a guide wire) for delivery through the vasculature system.

Once the curved portion 1604 is located at a desired location (e.g., in the superior vena cava SVC and the right atrium RA), the curved portion 1604 may be allowed to return to its predisposed curved shape. In this way, once the instrument body 1600 is oriented in an appropriate manner, the curved portion 1604 may serve to hold a portion 1606 of the instrument body 1600 against an area of a septal wall S where it is desired to puncture the septal wall S. As illustrated in FIG. 16, the curved shape of the portion 1604 also may cause another portion 1608 of the instrument body 1600 to lie against another wall W of the heart (e.g., an inner wall of the superior vena cava SVC). Consequently, the shape of the portion 1604, in conjunction with the engagement of the coronary sinus, may serve to more securely hold the portion 1606 of the instrument body 1600 at the desired location during deployment of a guide, during septal piercing or during other similar operations.

Figure 17:
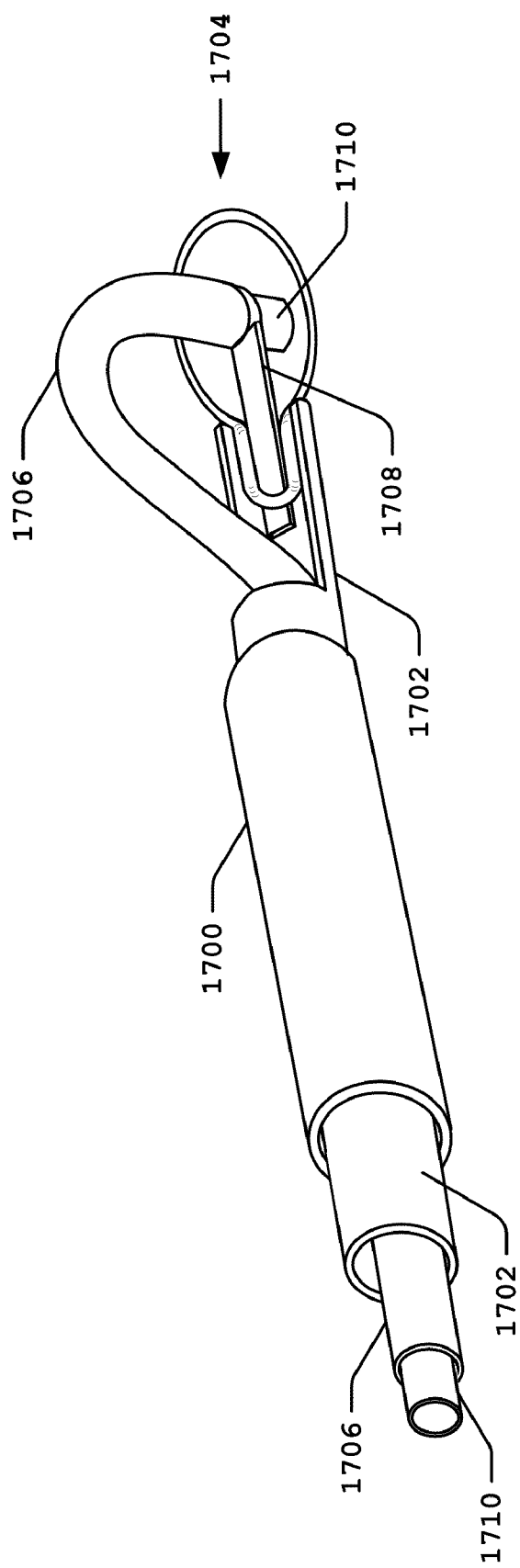
FIG. 17 is a simplified diagram of an embodiment of a delivery instrument.

FIG. 17 illustrates another embodiment of a delivery instrument comprising a catheter 1700. A structure 1702 is selectively extendable from the catheter 1700. The structure 1702 carries a resiliently expandable structure 1704. When the structures 1702 and 1704 are inside the catheter 1700 the structure 1704 is collapsed within the inner wall of the catheter 1700. When the structures 1702 and 1704 are extended from the catheter 1700 as shown in FIG. 17, the structure 1704 resiliently expands to a relatively large shape (e.g., a two-dimensional shape) as shown. This shape of the structure 1704 may be held relatively flat against an adjacent tissue surface (e.g. the septum), for example, by the action of the engagement of a portion of the catheter 1700 with a wall of the heart as shown in FIG. 16. In addition, in some implementations the delivery instrument 1700 may be incorporated into a main structure (e.g., component 116) that engages the coronary sinus as discussed above.

After the structure 1704 has been deployed, the structure 1706 may be pushed distally relative to the other components. The structure 1702 includes a component 1708 (e.g., a flexible structure) that prevents the distal end of the structure 1706 from passing beyond a desired point within the structure 1704. The engagement of the distal portion of the structure 1706 causes its distal portion to bend as shown in FIG. 17. This aims the distal end of the structure 1706 toward a desired tissue location and at a desired angle relative to the surface of that tissue. A tissue engaging (e.g., penetrating) structure 1710 may then be extended distally from the structure 1706 as shown in FIG. 17 to engage (e.g., penetrate) that tissue at the desired location and at the desired angle.

Figure 18:
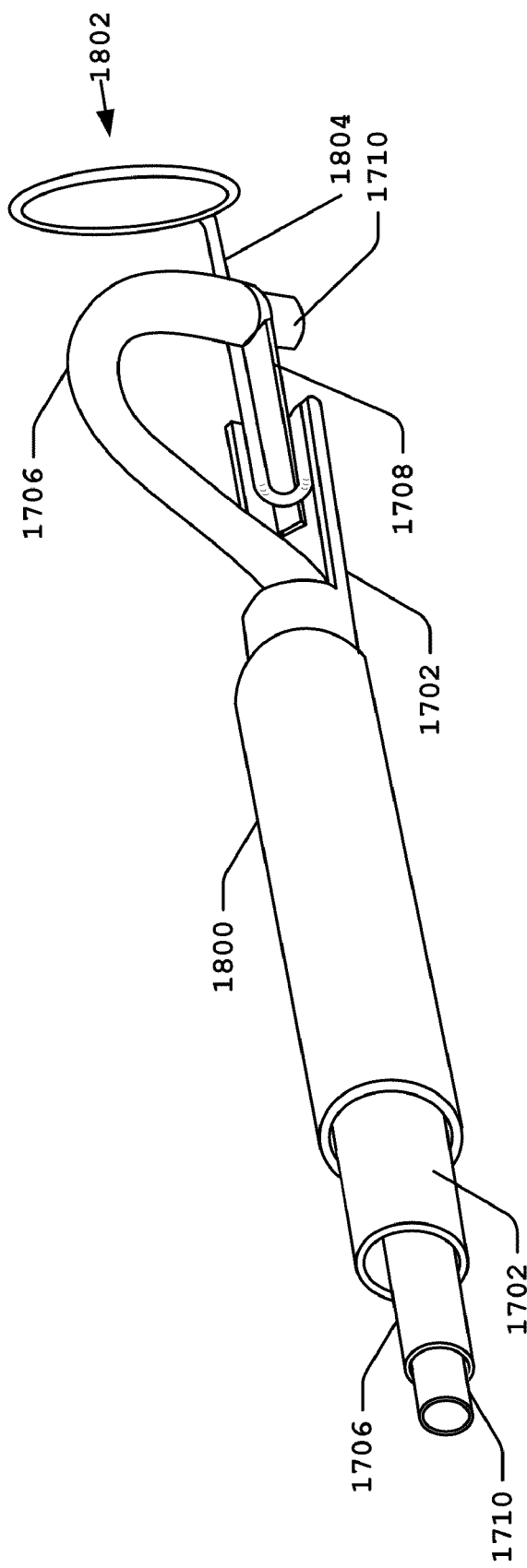
FIG. 18 is a simplified diagram of an embodiment of a delivery instrument.

FIG. 18 illustrates another embodiment of a delivery instrument comprising a catheter 1800. The catheter 1800 may include components 1702, 1706, 1708 and 1710 as in FIG. 17. However, in this embodiment the structure 1702 carries a resiliently expandable structure 1802 (e.g., attached to a portion 1804 of the structure 1802). When the structures 1702 and 1802 are inside the catheter 1800 the structure 1802 is collapsed within the inner wall of the catheter 1800. When the structures 1702 and 1802 are extended from the catheter 1800 as shown in FIG. 18, the structure 1802 resiliently expands to a relatively large shape (e.g., a two-dimensional shape) as shown. This shape of the structure 1802 may be adapted to engage the coronary sinus as discussed herein. For example, the structure 1802 may fit inside or may fit around the ostium of the coronary sinus. It should be appreciated that the structure 1802 may be implemented in other configurations (e.g., a different shape than depicted in FIG. 18) to engage the coronary sinus.

From the above it is should be appreciated that a delivery instrument constructed in accordance with the teachings herein may prove beneficial for certain transseptal implant procedures. Such a delivery instrument may be used, for example, to implant permanent transvenous leads as part of a pre-pectoral pacemaker, defibrillator, hemodynamic sensor system or other system into the left atrium or the left ventricle where a transseptal puncture across the inter-atrial septum is being performed from a superior transvenous approach via, for example, the jugular, subclavian or axillary veins.

Since most physicians that implant bi-ventricular pacing systems can reliably access the coronary sinus, having a delivery instrument for performing transseptal punctures across the inter-atrial septum that utilizes a coronary sinus catheter or similar structure as a platform provides a natural extension of the current techniques for implanting leads. Moreover, a coronary sinus catheter-based delivery apparatus as taught herein may be suitable for performing not only the traditional lead implantation into the coronary sinus venous system, but also a transseptal lead implantation in which a lead will be delivered across a septum into the left atrium or the left ventricle.

It should be appreciated from the above that the various structures and functions described herein may be incorporated into a variety of apparatuses (e.g., a catheter) and implemented in a variety of ways other those specifically described herein. Various structures may be used to implement the guide, the piercing instrument/guidewire, the seating structure, the catheters, the elongated member, the locking mechanisms, the markers and other components. For example, a guidewire as used herein may comprise a conventional guidewire or any elongated, flexible member that is suitable for guiding a component or device to an implant site or other site in a heart. In addition, various mechanisms may be used to guide a piercing instrument/guidewire to the septum. The components described herein may be constructed of various materials. For example, many of the components may be constructed of conventional implantable lead materials including polymers such as silicone or polyurethane or some other suitable material. Also, the components described herein may be oriented in a various ways. For example, a guide, a seating structure or a marker may be located at various positions or on various components at the distal end of the delivery instrument. The components described herein may be coupled (e.g., connected) in various ways using fasteners, adhesives, bonding techniques or other suitable mechanisms. The techniques described herein may be applicable to other walls of the heart and/or may be used to access other chambers of the heart.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

While certain exemplary embodiments have been described above in detail and shown in the accompanying drawings, it is to be understood that such embodiments are merely illustrative of and not restrictive of the broad invention. In particular, it should be recognized that the teachings of the invention apply to a wide variety of apparatuses and methods. It will thus be recognized that various modifications may be made to the illustrated and other embodiments described above, without departing from the broad inventive scope thereof. In view of the above it will be understood that the invention is not limited to the particular embodiments or arrangements disclosed, but is rather intended to cover any changes, adaptations or modifications which are within the scope and spirit of the invention as defined by the appended claims.

What is claimed is:

1. A method of providing access to a left side of a heart, comprising:

Routing a thin elongated delivery apparatus to the heart via a superior transvenous approach;

Positioning a distal portion of the delivery apparatus against tissue adjacent the ostium of the coronary sinus of the heart, wherein the distal portion of the delivery apparatus is adapted to maintain the distal portion of the delivery apparatus at said tissue adjacent the ostium of the coronary sinus; and Routing a piercing instrument through a guide on the delivery apparatus to create a hole in the inter-atrial septum of the heart, wherein the hole created in the inter-atrial septum is located proximal to the distal portion of the delivery apparatus.

2. The method of claim 1 wherein the distal portion of the delivery apparatus comprises at least one structural member extending from the delivery apparatus and adapted to engage the tissue adjacent the ostium of the coronary sinus.

3. The method of claim 2 wherein the at least one structural member comprises a plurality of tines adapted to expand from the delivery apparatus.

4. The method of claim 1 comprising expanding a plurality of tines from the distal portion of the delivery apparatus, wherein the positioning comprises seating the tines on the tissue adjacent to the ostium of the coronary sinus.

5. The method of claim 1 wherein the guide is adapted to carry a guidewire and a distal portion of the guide is positioned at a specified distance from the distal portion of the delivery apparatus.

6. The method of claim 1 wherein the guide is adapted to slideably carry at least one elongated member, the method comprising sliding the at least one elongated member to reorient the guide.

7. The method of claim 1 wherein a distal portion of the guide is positioned a fixed distance from the distal portion of the delivery apparatus.

8. The method of claim 1 wherein a distal portion of the guide is adapted to be positioned at different distances from the distal portion of the delivery apparatus, the method comprising adjusting a position of the distal portion of the guide relative to the distal portion of the delivery apparatus.

9. The method of claim 1 comprising rotating the delivery apparatus along a longitudinal axis to enable a distal end of the guide to be directed toward the inter-atrial septum.

10. The method of claim 1 wherein the delivery apparatus comprises a catheter adapted to carry at least one lead adapted for implant in the coronary sinus.

11. The method of claim 1 comprising implanting a lead, comprising a pressure sensor, in the hole.

12. The method of claim 1 comprising:
routing a guidewire through the guide and through the hole in the inter-atrial septum;
withdrawing the guide from the guidewire;
routing a dilator and sheath over the guidewire to expand the hole and extend the sheath into the hole;
removing the dilator and guidewire from the heart; and
routing a lead through the sheath to implant a distal portion of the lead in the hole in the inter-atrial septum.

13. The method of claim 1 wherein the distal portion of the delivery apparatus comprises at least one imaging marker, the method comprising substantially aligning the at least one imaging marker with the ostium of the coronary sinus.

14. The method of claim 1 wherein the distal portion of the delivery apparatus comprises tines comprising at least one imaging marker.

15. The method of claim 1 wherein a distal portion of the guide is positioned a defined distance from the distal portion of the delivery instrument that is positioned adjacent the ostium of the coronary sinus, such that the guide is adapted to be used to create the hole at or near the fossa ovalis of the heart.

16. The method of claim 1 wherein the guide is adapted to carry a lead.

* * * * *